United States Patent [19]

Poindexter

[11] Patent Number: 4,769,004
[45] Date of Patent: Sep. 6, 1988

[54] FLEXIBLE TUBING CLAMP AND METHOD OF USE

[75] Inventor: John H. Poindexter, Rochester, Minn.

[73] Assignee: MediVators, Inc., Rochester, Minn.

[21] Appl. No.: 20,447

[22] Filed: Mar. 2, 1987

[51] Int. Cl.[4] ............................................. A61M 1/00
[52] U.S. Cl. ................................... 604/33; 604/34; 604/249; 604/49; 251/4
[58] Field of Search ............... 604/33, 34, 49, 249, 604/250; 251/4; 222/528

[56] References Cited

U.S. PATENT DOCUMENTS

| | | | |
|---|---|---|---|
| 2,707,953 | 5/1955 | Ryan | 128/214 |
| 3,395,838 | 8/1968 | Beres et al. | 222/528 |
| 3,915,167 | 10/1975 | Waterman | 604/250 |
| 3,960,149 | 6/1976 | Bujan | 604/250 |
| 4,634,421 | 1/1987 | Hegemann | 604/34 |
| 4,689,043 | 8/1987 | Bisha | 604/249 |

Primary Examiner—C. Fred Rosenbaum
Assistant Examiner—J. L. Kruter
Attorney, Agent, or Firm—Kinney & Lange

[57] ABSTRACT

A clamp with a clamping body to accommodate a flexible hose extending through the bottom of a recess and bending over to lie along the bottom of the recess through a channel created by the recess with a slider movable thereover. The flexible tube can be used to provide access to a human stomach, being placed through the stomach wall by surgical methods with the clamp used to control flows therethrough.

21 Claims, 2 Drawing Sheets

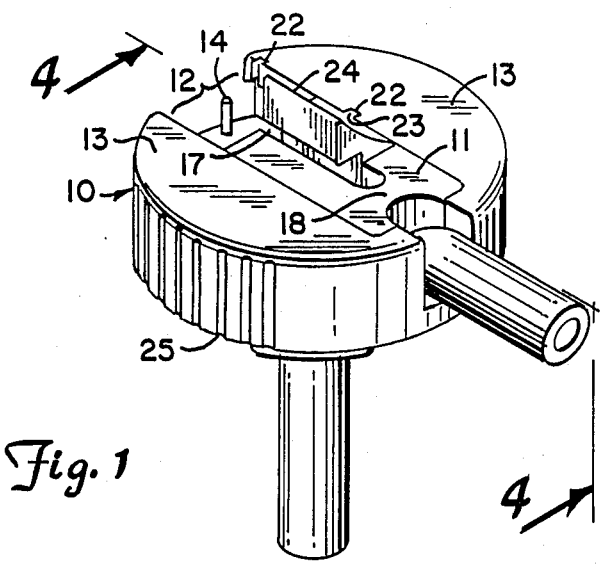
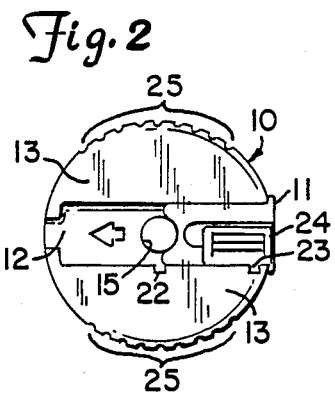
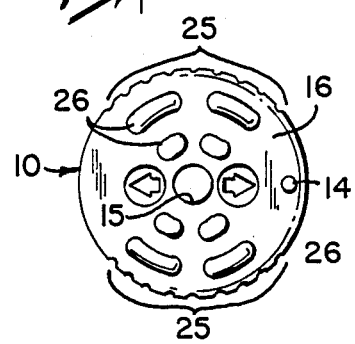
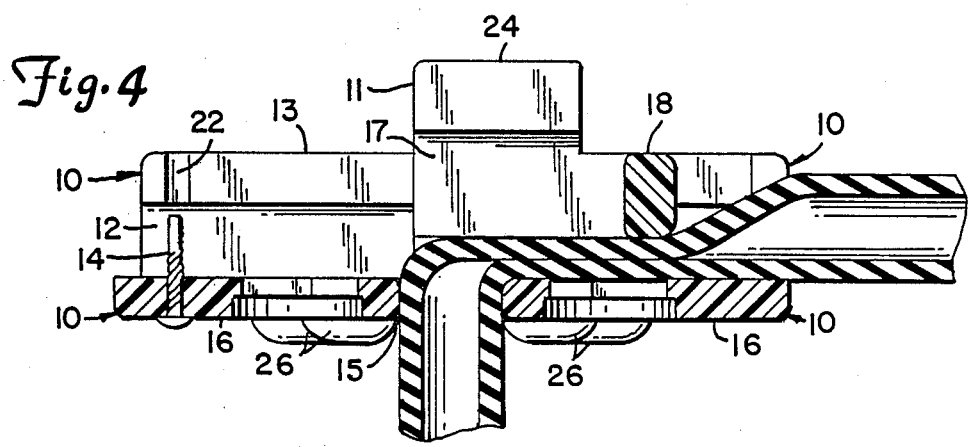
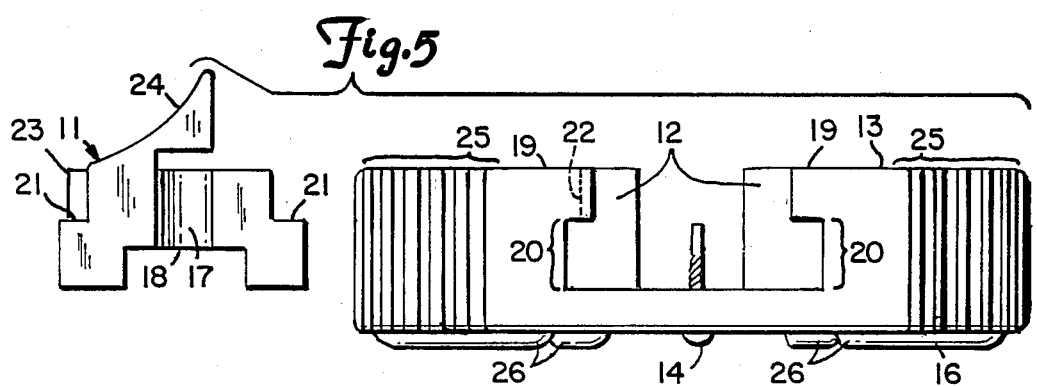

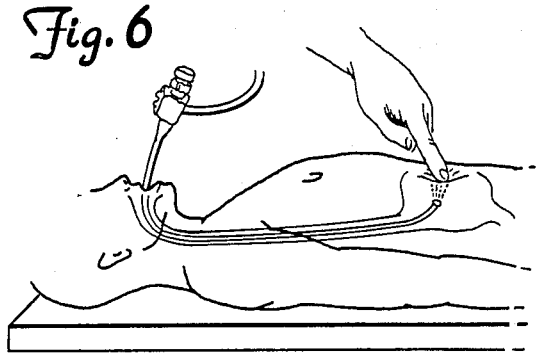
Fig. 6
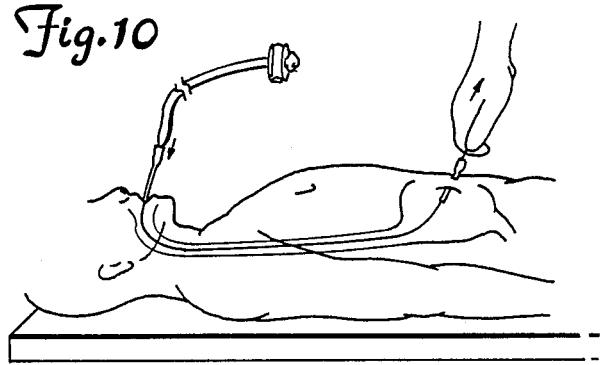
Fig. 10
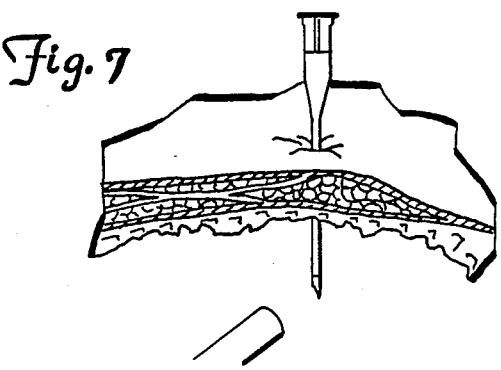
Fig. 7
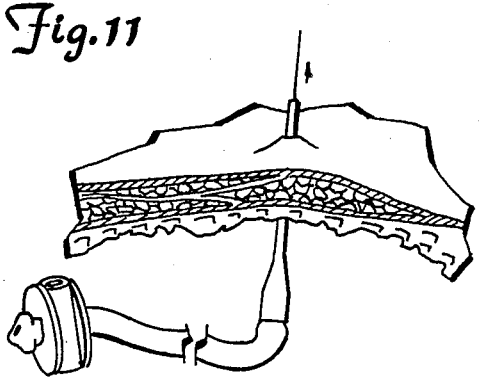
Fig. 11
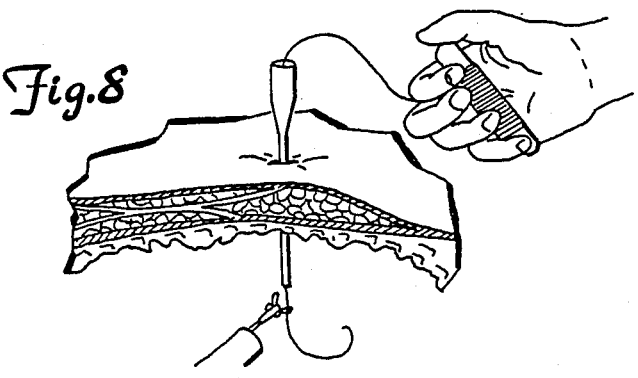
Fig. 8
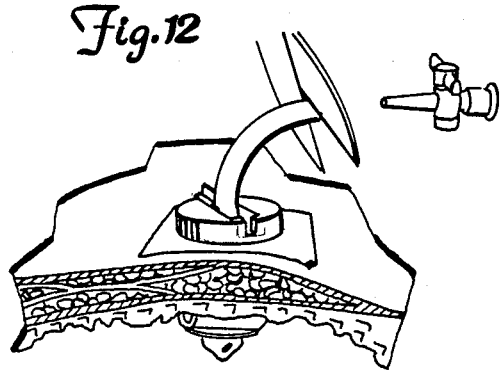
Fig. 12
Fig. 9
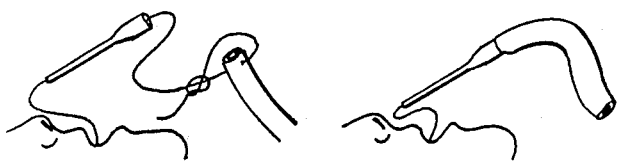

FLEXIBLE TUBING CLAMP AND METHOD OF USE

BACKGROUND OF THE INVENTION

1. Field of the Invention

The present invention relates to clamps for flexible tubes to control flow therethrough and, more particularly, to a clamp suitable for use with a catheter inserted into a human stomach through the adjacent abdominal wall.

Certain persons have the misfortune to be unable to take nutrition through their mouth intended to reach their stomachs. Such conditions can arise because of injury, because of growths along the route to the stomach, or because of neurological problems leading to impaired ability to swallow, or the like. Some of these people may benefit from having a catheter extending from outside the abdominal wall through both that wall and the stomach wall to extend into the stomach for providing nutrition directly to the stomach, i.e. a more or less permanent gastrostomy.

This can be done by placing a flexible tube, such as a latex tube, as a catheter through the abdominal wall and the stomach wall. Once such a catheter is in place, the portion of the tube extending outside the abdominal wall must have any material flows therethrough controlled. Typically, a clamp is used on the flexible tube to permit or deny flow therethrough as desired.

A desirable clamp for such a flexible tube in use for this purpose, or other direction liquid flow purpose, would be a single piece unit, in the sense that any piece parts therein cannot become separated, and would be operable through use of just one hand. Further, the clamping surface should be spread over a portion of the flexible tube to reduce or eliminate damage to, and fatigue of, the tube material which would otherwise be likely to occur from clamping confined to a single point.

SUMMARY OF THE INVENTION

The present invention provides a clamping body which can accommodate a flexible tube coming through the bottom of a recess, and bending over to lie along the bottom of the recess in the channel created by the recess, and finally out of the clamp. This bending of the tube occurs in response to a slider in the channel being moved along that channel over the tube on the channel floor in those instances when it is desired to close off the tube. In the opposite instances in which the tube is to be opened, the slider is moved in the opposite direction along the channel to a point exposing the opening in the channel floor from which the tube emerges.

The tube, if used to provide access to a human stomach, is placed through the stomach wall and abdominal wall by surgical methods. Thereafter, the clamp is placed over the tube for control of flow therethrough.

BRIEF DESCRIPTION OF THE DRAWINGS

FIG. 1 shows the clamp of the present invention in perspective, with a flexible tube inserted therein;

FIG. 2 shows a top view of the clamp without a tube therein;

FIG. 3 shows a bottom view of the clamp without a tube therein;

FIG. 4 shows a cross section view at the section line shown in FIG. 1;

FIG. 5 shows a cross section view at the section line shown in FIG. 2; and

FIGS. 6 through 12 show the results of steps taken in the method of placing a catheter through the stomach wall and abdominal wall and placing a clamp thereon to control flow therethrough.

DETAILED DESCRIPTION OF THE PREFERRED EMBODIMENTS

FIG. 1 shows the clamp of the present invention in position about a portion of a flexible tube, typically a latex tube serving as a part of a catheter. The clamp has a clamp body, 10, with a slider, 11, disposed therein. This slider is located in a channel, 12, which is formed by a recess provided in clamp body 10 inward from its upper major surface, 13. Channel 12 extends through clamp body 10 sufficiently far to the left to result in an open channel at that end. As a result, a pin, 14, is provided there to prevent slider 11 from coming out of channel 12 which would otherwise result in its separating from clamp body 10. Channel 12 also extends sufficiently far to the right in clamp body 10, as shown in FIG. 1, to be open on that end also. The opening, however, is narrowed by a narrowing of channel 12 at that end to prevent slider 11 from separating from clamp body 10 through that end of channel 12.

Turning to FIG. 2, a top view of the clamp is shown with slider 11 in a position at the right-hand end of channel 12 in that figure or the left-hand end of channel 12 with reference to FIG. 1. With slider 11 in this position, the flexible tube shown in FIG. 1 would not be clamped and complete flow therethrough would be possible. A passage, 15, is shown extending through clamp body 10 from the bottom surface of channel 12 through clamp body 10 to the major surface, 16, of clamp body 10 opposite major surface 13. Surface 16 is shown in FIG. 3 wherein passage 15 can be seen opening in this surface. The flexible tube shown in FIG. 1 has been eliminated from passage 15 in FIGS. 2 and 3, but in normal use the clamp would be slid over or away from a flexible tube going through passage 15.

In the arrangement just described, with slider 11 in the position shown in FIG. 2 and there being a flexible tube inserted in clamp passage 15 and out the bottom surface of channel 12, the clamp can be changed to stop fluid flow through the flexible tube by moving slider 11 all the way along channel 12 to a position immediately adjacent to the narrowed opening, as shown in FIG. 1. Slider 11, in being so moved, goes over the flexible tube, which is bent in response, to then lay along the bottom surface of channel 12, and then out the narrowed opening at the end of channel 12. This result can be more clearly seen in the cross section view indicated in FIG. 1 and shown in FIG. 4. Slider 11 with a slot, 17, extending therein from left to right, as shown in FIGS. 1 and 4, but stopping short of going all the way through to the right end, leaves a connecting bar, 18, between the two slot sides of slider 11. Moving slider 11 toward the narrowed opening end of channel 12 forces connecting bar 18 across the flexible tube pinching the tube closed against the bottom surface of channel 12. Thus, the flexible tube is bent as it comes out of passage 15 at the bottom surface of channel 12 and forced to lay along this surface, and to then extend through the narrowed opening of channel 12 on the right-hand side of FIGS. 1 and 4. This situation results in a clamped-together portion of the flexible tube extending all the way from the opening of passage 15 in the bottom surface of channel 12 to the narrowed opening at the end of channel 12. The flexible tube is thus forced together over a considerable distance rather than at one point when in the closed or no-flow state.

FIG. 5 shows drawings of the separate piece parts of the clamp. Channel 12 formed in clamp body 10 can be seen to have a bottom surface recessed from major surface 13 with a pair of lips, 19, overhanging a portion of this bottom surface but spaced apart therefrom. These spaces, 20, accept extended side portions or shoulders, 21, of slider 11 to prevent slider 11 from vertically leaving channel 12.

Indentation spaces, 22, are shown in one of lips 19 in FIGS. 1, 2 and 4, and by dashed line as a hidden feature in FIG. 5. A protuberance, 23, on the side of slider 11 fits in one of indentation spaces 22 if slider 11 has closed off the flexible tube fully by travelling the maximum distance toward the narrowed opening of channel 12. The protuberance its in the other indentation space 22 when the slider 11 has travelled to the opposite end sufficiently far to expose passage 15 and, as a result, open the flexible tube to flow therethrough. Protuberance 23 in either of indentation spaces 22 locks slider 11 in that position.

Protuberance 23 can be moved out of either indentation space 22 by pressure on a raised lever portion, 24, which permits bending the sides of slider 11 on either side of slot 17 (the slot sides) toward one another. This action on raised lever 24 can be accomplished by a thumb while the clamp body 10 is in the same hand. The holding of the clamp by a hand is made convenient by the provision of knurling, 25, along the edges of clamp body 10. Thus, single-hand operation is easy and convenient in view of clamp body 10 having nominal dimensions of 1½ inches in diameter by 9/16 of an inch thick.

Shown on surface 16 of clamp body 10 are further protusions, 26. Protrusions 26 act to keep surface 16 separated to some degree from the surface against which it rests, typically a sponge, to reduce perspiration and bacteria growth at that surface under surface 16. The material for clamp body 10 and slider 11 is an inert and tough engineering plastic based on acetyl resin.

Performance of a percutaneous endoscopic gastrostomy to insert a catheter to be controlled by the clamp proceeds by introducing a gastroscope into the patient's stomach. Air is then insufflated until the stomach folds disappear. The feeding tube site is located by transilluminating endoscopy light through the anterior abdominal wall. By use of downward pressure on the abdominal wall applied by a finger, a depression can be formed in the wall and the result viewed endoscopically, as shown in FIG. 6. Once the site is selected, a local anesthetic is infiltrated through the abdominal wall there.

An incision is made in the skin at the site of a size approximately that of the diameter of the catheter to be introduced. A 16-gauge Medicut needle with sheath is introduced through this incision into the lumen of the stomach under endoscopic vision, as shown in FIG. 7. The needle and syringe are removed leaving the Medicut sheath in place. No. 2 silk thread is passed through the sheath and grasped with a standard snare or biopsy forceps, as shown in FIG. 8. The endoscope is removed while maintaining a firm grasp on this thread as it is unrolled from its source, shown in FIG. 8 as a tube wrapped with a supply of the thread.

With the thread available through the mouth and wiped and dried, trim the thread at an angle and place a loose further Medicut sheath thereover with the narrow end pointed toward the mouth. A further Medicut needle is forced along a diameter through the tube end of a previously modified 16 Fr. Pezzer "mushroom" catheter. The needle and syringe are removed and the silk thread is also threaded through the sheath still in place in the catheter, as shown in FIG. 9. In the remaining step results shown in FIG. 9, the sheath is removed from the catheter leaving the thread through the catheter which is tied into a slip knot over the catheter and secured. Finally, the earlier threaded Medicut sheath is pulled up with the knot and the ends of the catheter contained in the wide end of the sheath.

The catheter is then lubricated and the entire catheter with the sheath thereon is pulled by hand through the mouth, esophogus, stomach and out through the abdomen as indicated in FIG. 10. Only the bumpers portion and mushroom head of the catheter remain in the stomach. The Medicut sheath acts as a tissue dilator for the catheter as it is pulled through the abdominal wall, as can be seen in FIG. 11.

The gastroscope is reinserted to observe the correct positioning of the bumpers of the catheter against the stomach wall, and that it is not too tight against that wall. A topical antibiotic is applied to the abdominal wound and is covered with a 3 inch×3 inch sponge. The clamp of FIG. 1 with slider 11 positioned to the left end thereof to expose passage 15 is slide over the tube of the catheter extending beyond the abdominal wall and sponge, the tube going through passage 15 and out the bottom surface of channel 12. The catheter is then cut to the desired length, as shown in FIG. 12. this completes installation of the catheter and the clamp. A further adapter may be placed on the end of the catheter for purposes of feeding. Clamp 15 can be operated by slider 11 to permit or deny any flow through the mushroom catheter.

While the foregoing arrangement description and the method of providing such an arrangement is an efficacious means of providing controlled access to a human stomach, such a clamp and tube can be applied also in other situations requiring a controlled, directed liquid flow. Although the present invention has been described with reference to preferred embodiments, workers skilled in the art will recognize that changes may be made in form and detail without departing from the spirit and scope of the invention.

What is claimed is:

1. A clamp for controlling flow through a flexible tube, said clamp comprising:

a clamp body having a channel therein having a longitudinal axis formed by a recess extending longitudinally therealong and inward from a first major surface to provide a channel bottom surface inward from said first major surface with said channel extending sufficiently in said clamp body so as to have at least one end thereof open to form a first channel end opening such that a selected flexible tube in which flow is to be controlled can be contained within said channel and can pass through said first channel end opening, said channel having a pair of lips extending from said clamp body substantially at said first major surface and substantially parallel to said longitudinal axis with one on either side thereof inwardly overhanging, but spaced apart from, said channel bottom surface, there being a passage through said clamp body which has an opening substantially contained within said channel bottom surface that is large enough to permit insertion of said selected flexible tubing through said passage and out said channel bottom surface; and a clamp slider having a pair of slide portions each of which extends into one of those spaces occurring between a said lip and said channel bottom surface, as aforesaid, with said clamp slider being spaced apart from said channel bottom surface between said slide portions, said clamp slider being movable along said channel from near said first channel end opening to at least a point toward that end of said channel opposite said first channel end opening so that moving aid clamp slider from near said channel end opening past said point substantially exposes said channel passage opening in said channel bottom surface.

2. The apparatus of claim 1 wherein said first channel end opening is narrowed sufficiently with respect to said channel to prevent said clamp slider from passing through said first channel end opening.

3. The apparatus of claim 1 wherein said channel extends sufficiently far in said clamp body to form a second channel end opening.

4. The apparatus of claim 3 wherein a pin is provided on said channel near said second channel end opening to block travel of said clamp slider.

5. The apparatus of claim 1 wherein said clamp body has a second major surface opposite said first major surface, said passage also opening in said second major surface.

6. The apparatus of claim 5 wherein said second major surface has a plurality of ventilation protrusions to permit some airflow along said second major surface.

7. The apparatus of claim 1 wherein said passage has a flexible tube therein which flexible tube is part of a mushroom catheter.

8. A clamp for controlling flow through a flexible tube, said clamp comprising:

a clamp body having a channel therein formed by a recess inward from a first major surface to provide a channel bottom surface inward from said first major surface with said channel extending sufficiently in said clamp body so as to have at least one end thereof open to form a first channel end opening such that a selected flexible tube in which flow is to be controlled can be contained within said channel and can pass through said first channel end opening, said channel having a a pair of lips with one on either side thereof overhanging, but spaced apart from, said channel bottom surface, with one of said lips having a first indentation space indented therein, there being a passage through said clamp body which has an opening substantially contained within said channel bottom surface that is large enough to permit insertion of said selected flexible tubing through said passage and out said channel bottom surface; and a clamp slider having a pair of slide portions each of which extends into one of those spaces occurring between a said lip and said channel bottom surface, as aforesaid, with said clamp slider being spaced apart from said channel bottom surface between said slide portions, said clamp slider being movable along said channel from near said first channel end opening to at least a point toward that end of said channel opposite said first channel end opening so that moving said clamp slider from near said channel end opening past said point substantially exposes said channel passage opening in said channel bottom surface, said clamp slider having a lock protrusion thereon which fits in said first indentation space if said clamp slider is substantially fully positioned towards said first channel end opening.

9. The apparatus of claim 8 wherein said clamp slider has a slot extending part way thereon to provide two slot side portions separated by said slot and has a raised lever portion on that one of said slot side portions having said lock protrusion for aid in pushing that said slot side portion toward that one remaining to remove said lock protrusion from said first indentation space.

10. The apparatus of claim 8 wherein one of said lips has a second indentation space indented therein and said lock protrusion fits in said second indentation space if said clamp slider is sufficiently positioned past said point of travel as aforesaid.

11. The apparatus of claim 10 wherein said clamp slider has a slot extending part way thereon to provide two slot side portions separated by said slot and has a raised lever portion on that one of said slot side portions having said lock protrusion for aid in pushing that slot side portion to remove said lock protrusion from a selected one of said first and second indentation spaces.

12. The apparatus of claim 8 wherein said first channel end opening is narrowed sufficiently with respect to said channel to prevent said clamp slider from passing through said first end channel opening.

13. The apparatus of claim 12 wherein said channel extends sufficiently far in said clamp body to form a second channel end opening.

14. The apparatus of claim 8 wherein said channel extends sufficiently far in said clamp body to form a second channel end opening.

15. The apparatus of claim 14 wherein said clamp body has a second major surface opposite said first major surface, said passage also opening in said second major surface.

16. The apparatus of claim 8 wherein said clamp body has a second major surface opposite said first major surface, said passage also opening in said second major surface.

17. A clamp for controlling flow through a flexible tube, said clamp comprising:

a clamp body having a channel therein formed by a recess inward from a first major surface to provide a channel bottom surface inward from said first major surface with said channel extending sufficiently in said clamp body so as to have at least one end thereof open to form a first channel end opening such that a selected flexible tube in which flow is to be controlled can be contained within said channel and can pass through said first channel end opening, said channel having a a pair of lips with one on either side thereof overhanging, but spaced apart from, said channel bottom surface, with one of said lips having a first indentation space indented therein, there being a passage through said clamp body which has an opening substantially contained within said channel bottom surface that is large enough to permit insertion of said selected flexible tubing through said passage and out said channel bottom surface; and a clamp slider having a pair of slide portions each of which extends into one of those spaces occurring between a said lip and said channel bottom surface, as aforesaid, with said clamp slider being spaced apart from said channel bottom surface between said slide portions, said clamp slider being movable along said channel from near said first channel end opening to at least a point toward that end of said channel opposite said first channel end opening so that moving said clamp slider from near said channel end opening past said point substantially exposes said channel passage opening in said channel bottom surface, said clamp slider having a lock protrusion thereon which fits in said first indentation space if said clamp slider is sufficiently positioned past said point of travel as aforesaid.

18. The apparatus of claim 17 wherein said clamp slider has a slot extending part way thereon to provide two slot side portions separated by said slot and has a raised lever portion on that one of said slot side portions having said lock protrusion for aid in pushing that said slot side portion toward that one remaining to remove said lock protrusion from said first indentation space.

19. A method for providing a controlled access to a space substantially enclosed by an enclosure structure having a wall formed substantially about said enclosed space, said method comprising:

forming an opening in said enclosure structure wall with said opening and sides thereof formed by said enclosure structure wall extending between regions external to said enclosure structure and said enclosed space;

providing a tubular access means through said enclosure structure opening to said enclosed space with said access means having a flexible tube emerging from said enclosure structure to said external regions;

preventing said tubular access means from being pulled into said external regions;

moving a clamp slider along a bottom surface of a channel formed in a clamp body of a clamp between a pair of overhanging lips and said channel bottom surface to expose a channel passage opening in said channel bottom surface; and placing said clamp about said tubular access means such that said tubular access means extends through said channel passage opening to control any passage therethrough.

20. The method of claim 19 further comprising inserting said access means into said enclosure structure opening from said enclosed space to result in said tubular access means emerging from said enclosure structure opening as aforesaid.

21. The method of claim 19 further comprising moving said clamp slider in an opposite direction along said channel bottom surface to thereby prevent any passage through said tubular access means.

* * * * *